(12) United States Patent
Miyabe et al.

(10) Patent No.: US 6,605,125 B2
(45) Date of Patent: Aug. 12, 2003

(54) HAIR DYE COMPOSITION

(75) Inventors: Hajime Miyabe, Tokyo (JP); Kenichi Matsunaga, Tokyo (JP); Yukihiro Ohashi, Tokyo (JP); Shintaro Totoki, Tokyo (JP); Yoshinori Saito, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/825,842

(22) Filed: Apr. 5, 2001

(65) Prior Publication Data

US 2001/0044976 A1 Nov. 29, 2001

(30) Foreign Application Priority Data

Apr. 7, 2000 (JP) .......................................... 2000-107185
Jun. 27, 2000 (JP) .......................................... 2000-193183

(51) Int. Cl.[7] .............................................. A61K 7/13
(52) U.S. Cl. ....................... 8/405; 8/401; 8/409; 8/410; 8/411; 546/166
(58) Field of Search ........................... 8/401, 405, 409, 8/410, 411; 546/166

(56) References Cited

U.S. PATENT DOCUMENTS

| 4,168,144 A | 9/1979 | Curry et al. | 8/10.01 |
| 4,260,770 A | 4/1981 | Schwander et al. | 548/159 |
| 4,332,937 A | 6/1982 | Zink | 544/105 |
| 4,598,151 A | 7/1986 | Kuehlthau et al. | 546/167 |
| 5,474,578 A | 12/1995 | Chan et al. | 81/481 |
| 5,520,707 A | 5/1996 | Lim et al. | 8/426 |
| 5,733,343 A | 3/1998 | Moeckli | 8/426 |
| 5,879,412 A | 3/1999 | Rondeau et al. | 8/411 |
| 5,888,252 A | 3/1999 | Moeckli | 8/426 |
| 5,980,587 A | 11/1999 | Samain | 8/426 |

FOREIGN PATENT DOCUMENTS

| DE | 1 569 660 | 1/1971 |
| DE | 37 38 027 | 5/1988 |
| EP | 0 017 621 | 10/1980 |

(List continued on next page.)

*Primary Examiner*—Mark Kopec
*Assistant Examiner*—Eisa Elhilo
(74) *Attorney, Agent, or Firm*—Oblon, Spivak, McClelland, Maier & Neustadt, P.C.

(57) ABSTRACT

Provided is a hair dye composition comprising as a direct dye a compound represented by the following formula (1), (2), (3) or (4):

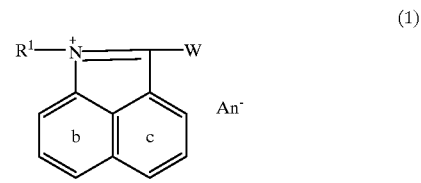

(1)

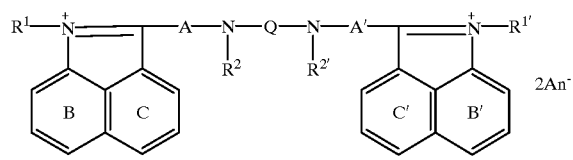

(2)

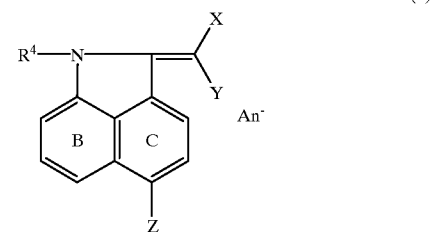

(3)

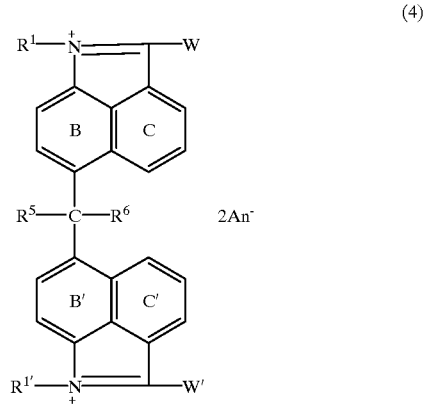

(4)

[wherein, $R^1$ and $R^{1'}$ each independently represents a (substituted) $C_{1-6}$ alkyl or a (substituted) aryl group; W and W' each independently represents a group —A—$NR^2R^3$ or a (substituted) heterocyclic aromatic group; A and A' each independently represents a divalent (substituted) aryl group; $R^2$, $R^{2'}$ and $R^3$ each independently represents H, a (substituted) alkyl or a (substituted) aryl group, or $R^2$, $R^{2'}$ or $R^3$ may be bonded to A or A', thereby forming a heterocycle, $R^2$ and $R^3$, or $R^2$ and $R^{2'}$ are coupled to form a heterocycle, together with the adjacent atom; $R^4$ to $R^6$ each independently represents H, (substituted) alkyl or (substituted) alkenyl group; Q represents a divalent organic group; X represents a modified carboxy group, an —$SO_2$—T— group (in which, T represents an alkyl, alkenyl or aryl) or a heterocyclic group; Y represents a CN— or heterocyclic group; Z represents a cationic group, and $An^-$ represents an anion). The hair dye composition according to the present invention has markedly high hair dyeing power, has less color fade over time and undergoes a small color tone change in the dye even after storage.

17 Claims, No Drawings

U.S. PATENT DOCUMENTS

| | | |
|---|---|---|
| GB | 1 583 160 | 1/1981 |
| JP | 47-009107 | 5/1972 |
| JP | 49108378 A * | 10/1974 |
| JP | 49-108378 | 10/1974 |
| JP | 51-008317 | 1/1976 |
| JP | 53-027626 | 3/1978 |
| JP | 53-027627 | 3/1978 |
| JP | 55-135169 | 10/1980 |
| JP | 58-2204 | 1/1983 |
| JP | 58-103561 | 6/1983 |
| JP | 63-135458 | 6/1988 |
| JP | 6-271435 | 9/1994 |
| JP | 8-501322 | 2/1996 |
| JP | 8-507545 | 8/1996 |
| JP | 9-118832 | 5/1997 |
| JP | 10-502946 | 3/1998 |
| JP | 10-194942 | 7/1998 |
| WO | WO 95/15144 | 6/1995 |

* cited by examiner

HAIR DYE COMPOSITION

TECHNICAL FIELD

The present invention relates to a hair dye composition which has markedly high dyeing power, can impart the hair with a remarkably vivid color ranging from red to blue, has less color fade over time and undergoes a small color tone change in the dye even after storage.

BACKGROUND ART

Hair dyes can be classified by the dye to be used therefor, or whether they have bleaching action of melanin or not. Typical examples include a two-part permanent hair dye composed of a first part containing an alkali agent, an oxidation dye and a direct dye such as nitro dye and a second part containing an oxidizing agent; and one-part semi-permanent hair dye containing an organic acid or an alkali agent, and a direct dye such as acid dye, basic dye or nitro dye.

The above-described permanent hair dye is however accompanied with the drawbacks that color tone imparted by an oxidation dye is not so vivid and the color of the hair dyed with a vivid-color producing nitro dye ordinarily employed as a direct dye markedly fades over time and becomes dull soon even if the color tone rightly after dyeing is very vivid (Japanese Patent Application Laid-Open (Kokai) No. Hei 6-271435).

Recently, hair dyes containing as a direct dye a so-called cationic dye having a cation group contained in their conjugate system have been reported (Japanese Language Laid-Open Publication (PCT) No. Hei 8-507545, 8-501322 or 10-502946, or Japanese Patent Application Laid-Open (Kokai) No. Hei 10-194942). They have however been found to involve drawbacks that intended dyeing effects are not available owing to decomposition of them caused by mixing, upon hair dyeing, with hydrogen peroxide ordinarily employed as an oxidizing agent; and that when the cation group is incorporated in an azo(—N=N—)-based conjugated system, they are unstable to an alkali agent or a reducing agent essentially contained in a permanent hair dye.

DISCLOSURE OF THE INVENTION

An object of the present invention is to provide a hair dye composition featuring high hair dyeing power, less color fade over time and excellent storage stability not permitting a large color tone change of the dye after storage.

The present inventors have found that a hair dye composition containing the below-described compound—which is known as a dye for dyeing or printing therewith fiber materials, paper or leather and is, for example, described in Japanese Patent Application Laid-Open (Kokai) No. Sho 47-9107, Japanese Patent Application Laid-Open (Kokai) No. Sho 49-108378, Japanese Patent Application Laid-Open (Kokai) No. Sho 51-8317, Japanese Patent Application Laid-Open (Kokai) No. Sho 53-27626, Japanese Patent Application Laid-Open (Kokai) No. Sho 53-27627, Japanese Patent Application Laid-Open (Kokai) No. Sho 55-135169, Japanese Patent Application Laid-Open (Kokai) No. Sho 63-135458, German Patentschrift DE 1569660, or Japanese Patent Application Laid-Open (Kokai) No. Sho 58-103561—can dye the hair with high dyeing power without causing decomposition of the dye upon hair dying, can strongly impart the hair with a markedly vivid color ranging from red to blue, exhibits excellent light resistance, washing resistance, perspiration resistance, friction resistance and weather resistance, and undergoes a smaller change in color tone of the dye after storage as compared with that rightly after preparation because the dye exists in the composition stably.

In one aspect of the present invention, there is thus provided a hair dye composition comprising, as a direct dye, a compound represented by the following formula (1), (2), (3) or (4):

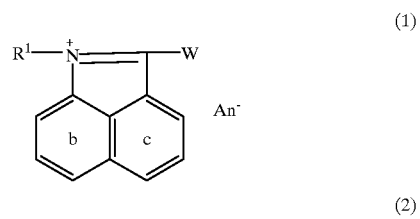

(1)

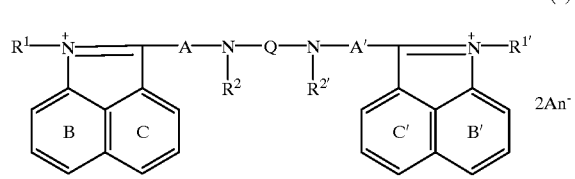

(2)

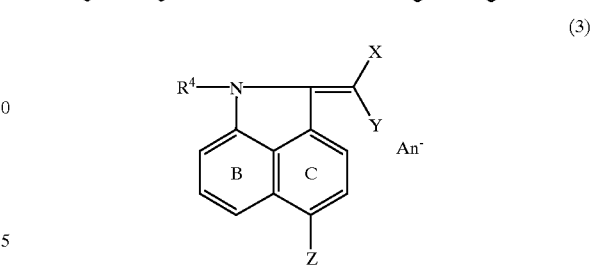

(3)

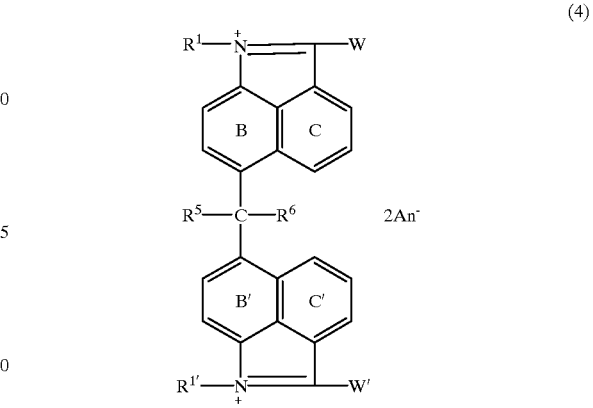

(4)

[wherein, $R^1$ and $R^{1'}$ each independently represents a $C_{1-6}$ alkyl group which may have a substituent or an aryl group which may have a substituent;

W and W' each independently represents a group —A—$NR^2R^3$ or a heterocyclic aromatic group which may have a substituent;

A and A' each independently represents a divalent aryl group which may have a substituent;

$R^2$, $R^{2'}$ and $R^3$ each independently represents a hydrogen atom, a $C_{1-6}$ alkyl group which may have a substituent or an aryl group which may have a substituent; or $R^2$, $R^{2'}$ or $R^3$ may be bonded to A or A', thereby forming a nitrogen-containing heterocycle, $R^2$ and $R^3$ are coupled to form a nitrogen-containing heterocycle, together with the adjacent nitrogen atom, or $R^2$ and $R^{2'}$ are coupled to form a nitrogen-containing heterocycle together with the adjacent two nitrogen atoms and Q;

$R^4$, $R^5$ and $R^6$ each independently represents a hydrogen atom, a $C_{1-6}$ alkyl group which may have a substituent or $C_{2-6}$ alkenyl group which may have a substituent;

Q represents a divalent organic connecting group;

X represents a modified carboxy group, an —SO$_2$—T— group (in which, T represents a $C_{1-4}$ alkyl group, $C_{2-4}$ alkenyl group or an aryl group) or a heterocyclic group;

Y represents a cyano group or a heterocyclic group;

Z represents a cationic group, rings b, c, B, C, B' and C' each independently may have a substituent other than that described directly in the formula, or when in the formula (1), $R^1$ represents a $C_{1-6}$ alkyl group and W represents a group —A—NR$^2$R$^3$ (except that $R^2$ or $R^3$ is coupled with A to form a nitrogen-containing heterocycle), any one of the rings b, c and A has at least one substituent; and An$^-$ represents an anion).

In another aspect of the present invention, there is also provided a hair dyeing method which comprises appying the above-described hair dye composition to the hair.

BEST MODE FOR CARRYING OUT THE INVENTION

In the formulas (1) to (4), examples of the $C_{1-6}$ alkyl group as $R^1$, $R^{1'}$, $R^2$, $R^{2'}$, $R^3$, $R^4$, $R^5$ or $R^6$ include methyl, ethyl, propyl, isopropyl and cyclohexyl groups, which may each be substituted by an aryl, alkoxy, amino, hydroxyl or cyano group, or a halogen atom.

In the formulas (1), (2) and (4), examples of the aryl group as $R^1$, $R^{1'}$, $R^2$, $R^{2'}$ or $R^3$ include phenyl and naphthyl groups, which may each be substituted by an alkyl, aryl, alkoxy, amino, dialkylamino, hydroxyl, cyano or nitro group, of a halogen atom, more specifically, methyl, ethyl, methoxy, ethoxy or diethylamino group, or a chlorine or bromine atom.

In the formulas (3) and (4), examples of the $C_{2-6}$ alkenyl group as $R^4$, $R^5$ or $R^6$ include ethenyl and propenyl groups, which may each be substituted by a cyano or phenyl group.

In the formulas (1), (2) and (4), examples of the divalent aryl group as A or A' include phenylene and naphthylene groups. In the formulas (1) and (4), examples of the heterocyclic aromatic group as W or W' include indolyl, particularly 3-indolyl group, which may be substituted by an alkyl, aryl, alkoxy, amino, hydroxyl, cyano or nitro group, or a halogen atom, more specifically, a methyl, ethyl, methoxy or ethoxy group, or a chlorine or bromine atom.

In the formula (2), the below-described groups can be mentioned as examples of the divalent organic connecting group represented by Q.

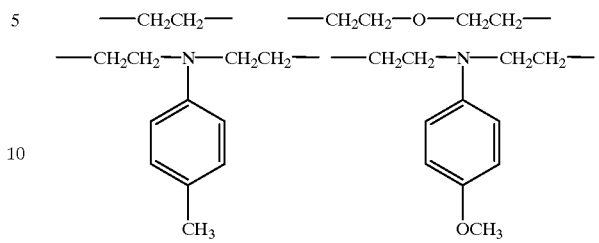

In the formula (3), examples of the modified carboxy group as X include cyano, alkylcarbamoyl and acyl groups.

In the formula (3), examples of the heterocyclic group as X or Y include the following groups:

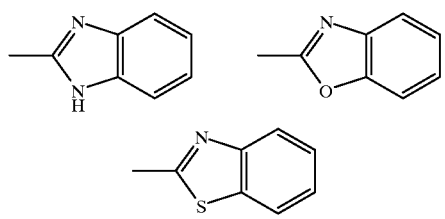

In the formula (3), examples of the cationic group as Z include trialkylammoniumyl groups such as trimethylammnoiumyl and triethylammoniumyl, pyridyl group and alkylcarbamoyl groups having these groups bonded thereto.

In the formulas (1) to (4), examples of the substituent for the rings b, c, B, C, B' or C' include alkyl, alkenyl, aryl, alkoxy, amino and carbamoyl groups which may each have a substituent, hydroxyl group, cyano group, nitro group and halogen atoms. Specific examples include methyl group, ethyl group, methoxy group, ethoxy group, chlorine atom, bromine atom, dimethylamino group, N,N-diethylcarbamoyl group, piperidinocarbonyl group, cyanoethenyl group, cyanopropenyl group and ethylsulfonylethenyl group.

In the formulas (1) to (4), examples of the anion represented by An$^-$ include chloride ions, bromide ions, iodide ions, trichlorozincic acid ions, tetrachlorozincic acid ions, sulfuric acid ions, hydrogensulfuric acid ions, methyl sulfate ions, phosphoric acid ions, formic acid ions and acetic acid ions.

The following are specific examples of the direct dyes (1) to (4) to be used in the present invention:

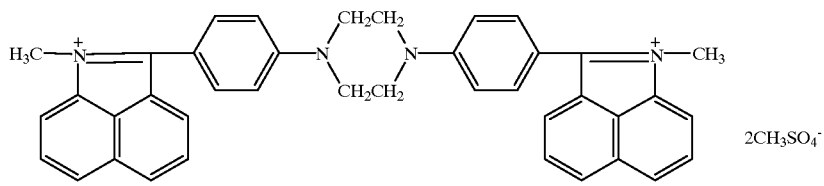

-continued
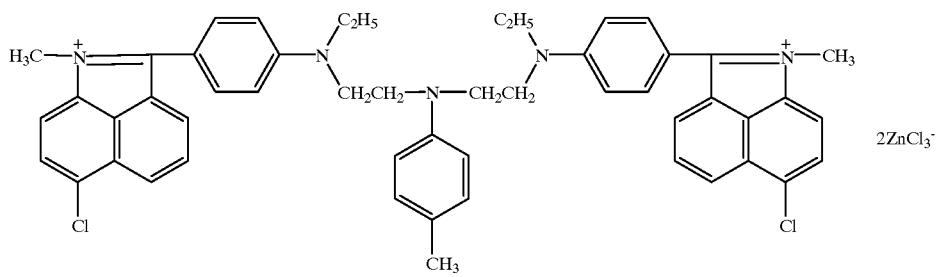
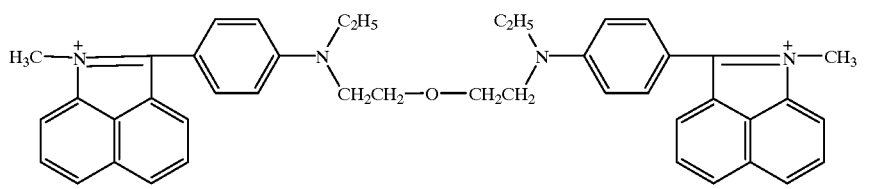
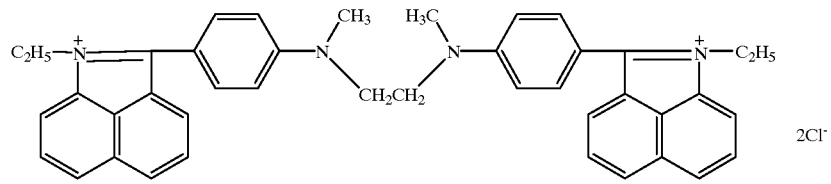
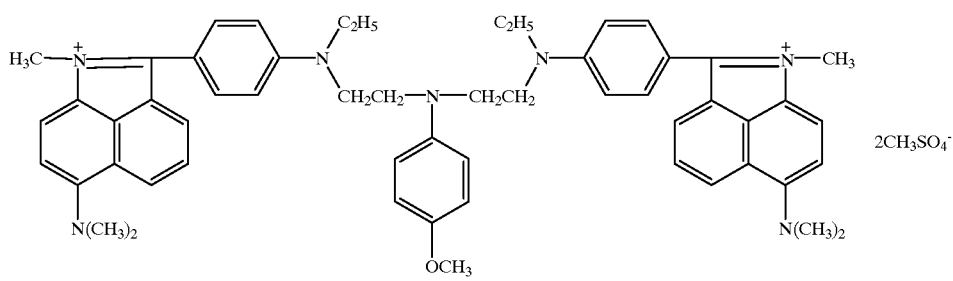
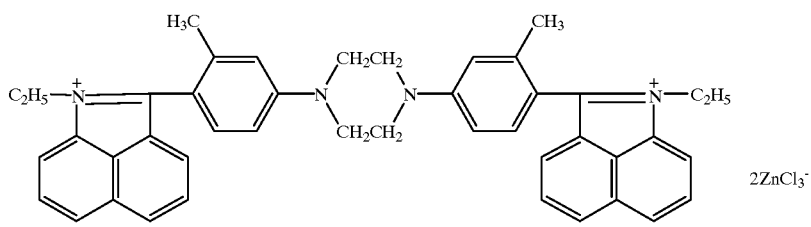
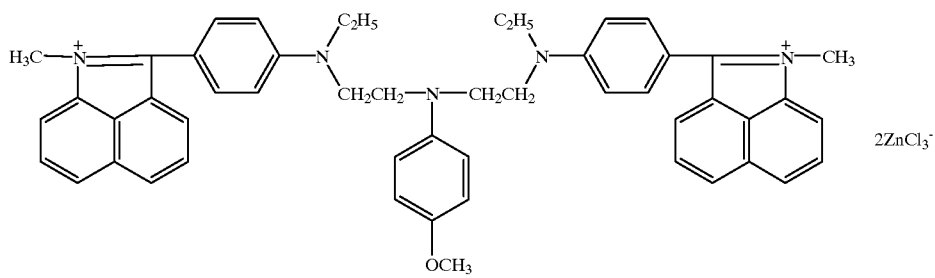
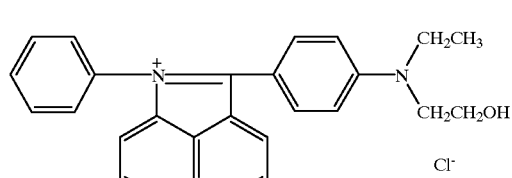
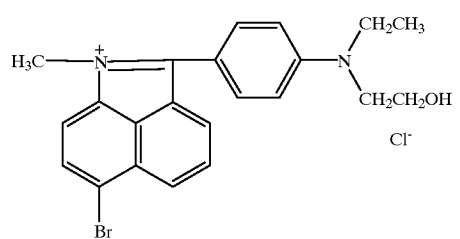

-continued
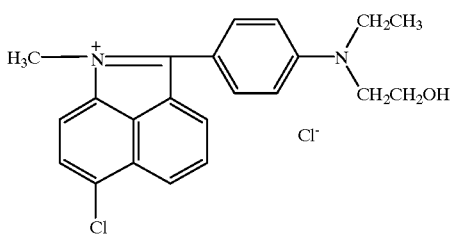
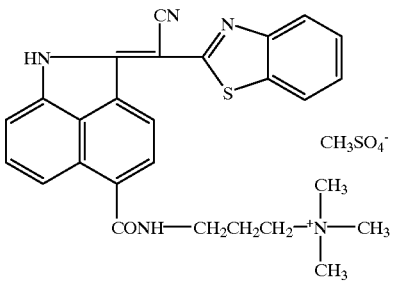
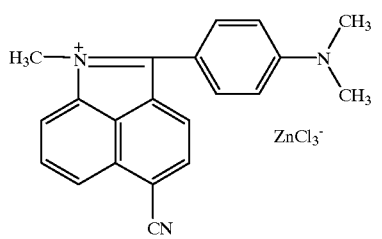
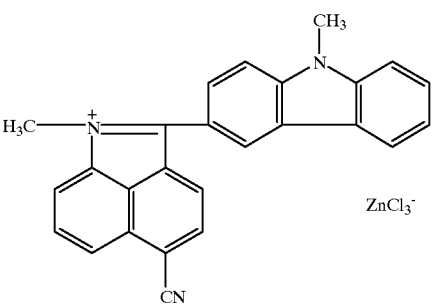
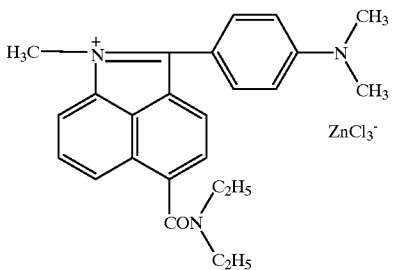
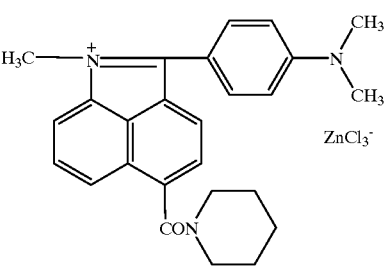
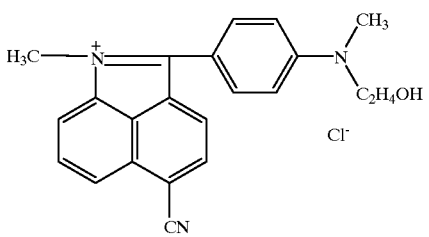
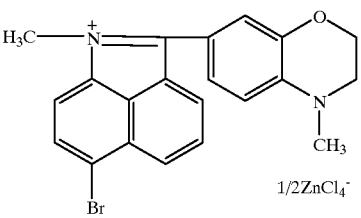
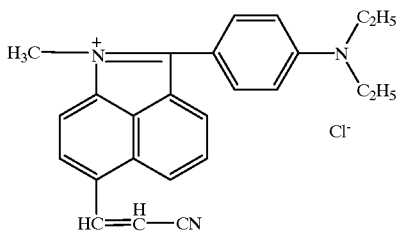
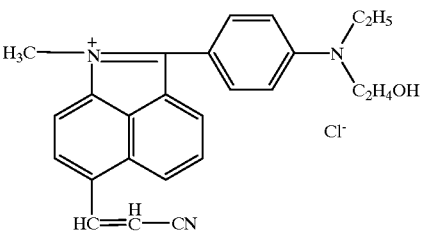
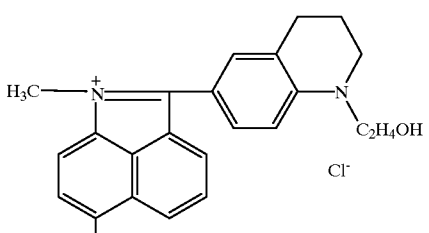
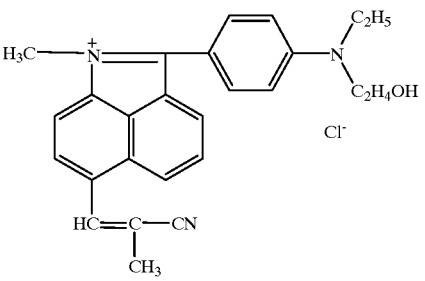

-continued

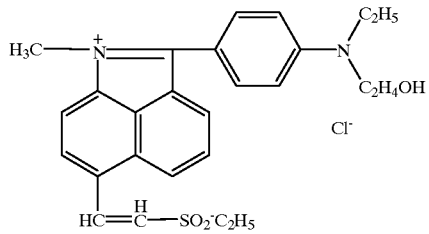

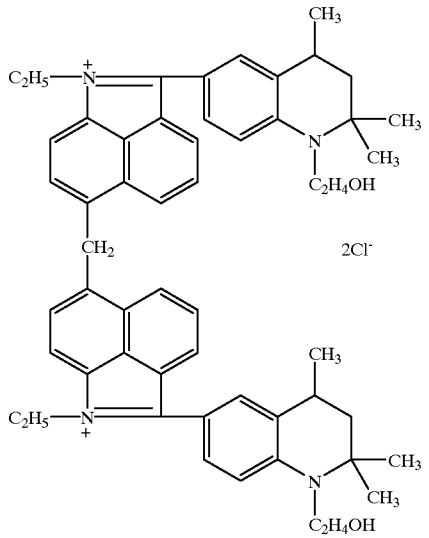

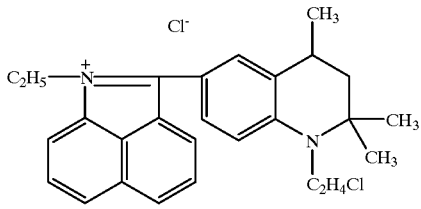

As the direct dyes (1) to (4), one or more can be used. Alternatively, another direct dye can be used in combination. The combination of the direct dye of the present invention with red and blue dyes makes it possible to dye the hair with a deep and highly lustrous dark brown or black color.

Examples of the direct dye other than the direct dyes (1) to (4) include Basic Blue 7 (C.I. 42595), Basic Blue 26 (C.I. 44045), Basic Blue 99 (C.I. 56059), Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 22 (C.I. 11055), Basic Red 76 (C.I. 12245), Basic Red 118 (C.I. 12251:1) and Basic Yellow 57(C.I. 12719); and basic dyes as described in Japanese Patent Publication No. Sho 58-2204, Japanese Patent Application Laid-Open No. Hei 9-118832, Japanese Language Laid-Open Publication (PCT) No. Hei 8-501322 or Japanese Language Laid-Open Publication (PCT) No. Hei 8-507545.

The direct dyes (1) to (4) are each preferably added in an amount of 0.01 to 20 wt. %, more preferably 0.05 to 10 wt. %, especially 0.1 to 5 wt. % based on the whole composition (after mixing of all the parts when a two-part or three-part composition is employed; this will apply equally hereinafter). When another direct dye is used in combination, the content of it in total with the direct dye of the present invention preferably ranges from 0.05 to 10 wt. %, especially 0.1 to 5 wt. % based on the whole composition.

The hair dye composition of the present invention is preferably adjusted to pH 6 to 11, with pH 8 to 11 being more preferred. Examples of the alkali agent to be used for pH adjustment include ordinarily employed ones such as ammonia, organic amines and salts thereof. The alkali agent is preferably added in an amount of 0.01 to 20 wt. %, more preferably 0.1 to 10 wt. %, especially 0.5 to 5 wt. % based on the whole composition.

In the hair dye composition of the present invention, an oxidizing agent can be incorporated. In this case, hair dyeing and bleaching can be carried out simultaneously, which facilitates more vivid hair dyeing. Ordinarily employed oxidizing agents, for example, hydrogen peroxide, persulfates such as ammonium persulfate, potassium persulfate and sodium persulfate, perborates such as sodium perborate, percarbonates such as sodium percarbonate and bromates such as sodium bromate and potassium bromate are usable. Out of them, hydrogen peroxide is especially preferred. The oxidizing agent is added in an amount of 0.5 to 10 wt. %, especially 1 to 8 wt. % based on the whole composition.

In the hair dye composition of the present invention, an oxidation dye can be incorporated further. In this case, this incorporation enables remarkably vivid dyeing not attainable by the single use of an oxidation dye. As the oxidizing agent, the above-exemplified ones can be used, with hydrogen peroxide being particularly preferred. Alternatively, an oxidizing enzyme such as laccase can be employed. As the oxidation dye, known developers and couplers ordinarily employed for an oxidation type hair dye can be used.

Examples of the developer include p-phenylenediamines having one or several groups selected from $NH_2$—, NHR— and $NR_2$-groups (in which, R represents a $C_{1-4}$ alkyl or hydroxyalkyl group) such as p-phenylenediamine, p-toluylenediamine, N-methyl-p-phenylenediamine, chloro-p-phenylenediamine, 2-(2'-hydroxyethylamino)-5-aminotoluene, N,N-bis-(2-hydroxyethyl)-p-phenylenediamine, 2-hydroxyethyl-p-phenylenediamine, 2,6-dimethyl-p-phenylenediamine, methoxy-p-phenylenediamine, 2,6-dichloro-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine and N-2- methoxyethyl-p-phenylenediamine; 2,5-diaminopyridine derivatives and 4,5-diaminopyrazole derivatives; p-aminophenols such as p-aminophenol, 2-methyl-4-aminophenol, N-methyl-p-aminophenol, 3-methyl-4-aminophenol, 2,6-dimethyl-4-aminophenol, 3,5-dimethyl-4-aminophenol, 2,3-dimethyl-4-aminophenol and 2,5-dimethyl-4-aminophenol; o-aminophenols, o-phenylenediamines, 4,4'-diaminophenylamine and hydroxypropylbis(N-hydroxyethyl-p-phenylenediamine); and salts thereof.

Examples of the coupler include 1-naphthol, 1,5-dihydroxynaphthalene, 1,7-dihydroxynaphthalene, 2,7-dihydroxynaphthalene, 5-amino-2-methylphenol, 5-(2'-hydroxyethylamino)-2-methylphenol, 2,4-diaminoanisole, m-toluylenediamine, resorcin, m-plenylenediamine, m-aminophenol, 4-chlororesorcin, 2-methylresorcin, 2,4-diaminophenoxyethanol, 2,6-diaminopyridine, 2-amino-3-hydroxypyridine, 4-hydroxyindole, 6-hydroxyindole, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine and 1,3-bis(2,4-diaminophenoxy)propane; and salts thereof.

As each of the developer and coupler, one or more can be used. Although no particular limitation is imposed on the content of the developer or coupler, it is preferably added in an amount of 0.01 to 20 wt. %, especially 0.5 to 10 wt. % based on the whole composition.

To the hair dye composition of the present invention, a known autoxidation dye typified by an indole or an indoline, or a known direct dye such as a nitro dye or a disperse dye can also be added.

When an anionic component (such as anionic surfactant or anionic polymer) is added to the hair dye composition of the present invention, it is preferred to satisfy the following equation:

"Ion activity concentration of the anionic component/ion activity concentration of the cationic direct dye (1), (2), (3) or (4)≦8"

The term "ion activity concentration" as used herein means "molar concentration×ionic valence"

Addition of a polyol, polyol alkyl ether, cationic or amphoteric polymer or silicone to the hair dye composition of the present invention is preferred for bringing about uniform hair dyeing effects and improvement in cosmetic effects.

In addition to the above-described components, those ordinarily employed as a raw material for cosmetics can be added to the hair dye composition of the present invention. Examples of such an optional component include hydrocarbons, animal or vegetable fats and oils, higher fatty acids, organic solvents, penetration promoters, cationic surfactants, natural or synthetic polymers, higher alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes and ultraviolet absorbers.

The hair dye composition of the present invention can be prepared in a conventional manner into a one-part composition, a two-part composition having a first-part component containing an alkali agent and a second-part component containing an oxidizing agent or a three-part composition having, in addition to these two components, a powdery oxidizing agent such as persulfate. The direct dyes (1), (2), (3) and (4) can each be incorporated in either one or both of the part components of the two-part or three-part composition. The one-part type is applied to the hair directly, while the two- or three-part type is applied to the hair after mixing the components upon hair dyeing.

No particular limitation is imposed on the form of the hair dye composition of the present invention. Examples include powder, transparent, liquid, emulsion, cream, gel, paste, aerosol, and aerosol foam. It preferably has a viscosity of 2000 to 100000 mPa.s when it is applied to the hair (after mixing of all the components when a two-part or three-part type composition is employed).

EXAMPLES

Compounds employed in the below-described examples are as follows:

Compound (a)

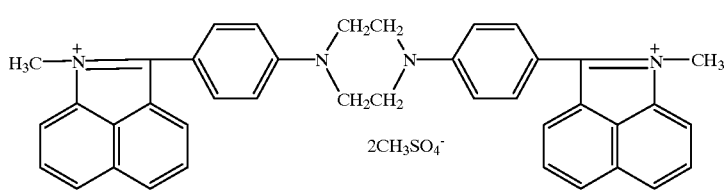

Compound (b)

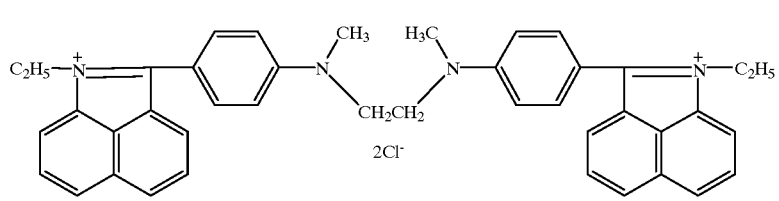

-continued
Compound (c)
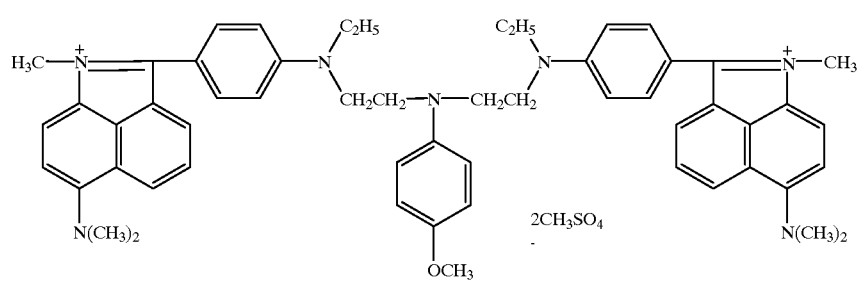
Compound (d)
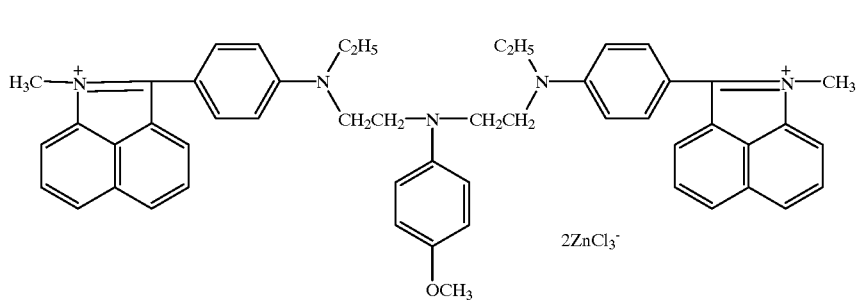
Compound (e)             Compound (f)
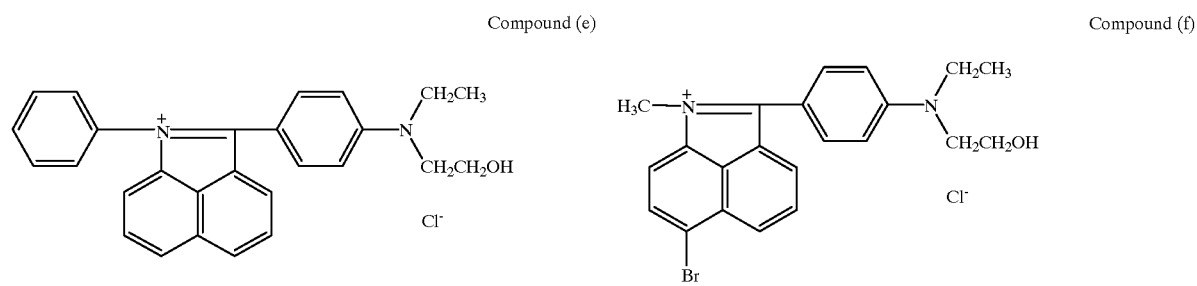
Compound (g)             Compound (h)
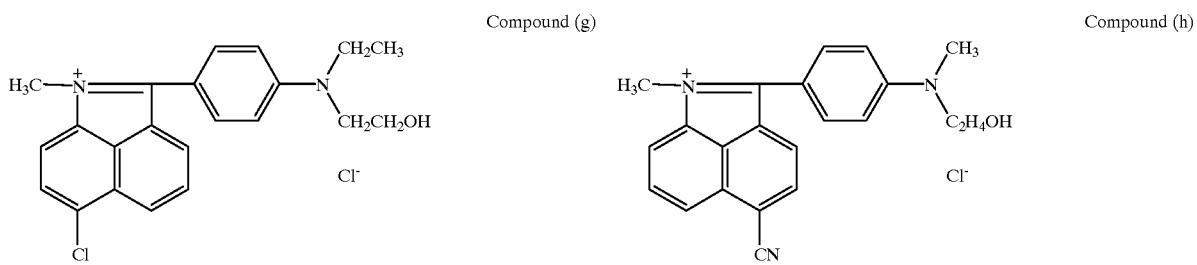
Compound (i)             Compound (j)
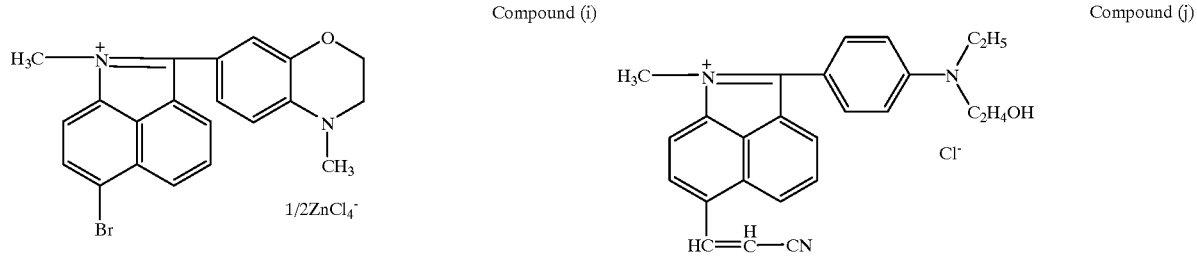
Compound (k)

Examples 1 to 5

In a manner known per se in the art, hair dye compositions as shown in Table 1 were prepared.

TABLE 1

| (wt. %) | Example 1 | 2 | 3 | 4 | 5 |
|---|---|---|---|---|---|
| Dye [Compound (f)] | 0.2 | | | 0.1 | |
| Dye [Compound (i)] | | 0.5 | | 0.1 | 0.2 |
| Dye [Compound (a)] | | | 0.3 | | |
| Dye [Compound (k)] | | | | 0.2 | 0.05 |
| Ethanol | | 5 | | 5 | 5 |
| Propylene glycol | | | 5 | | 5 |
| Diethylene glycol monoethyl ether | | 10 | | | |
| Guar gum | 1 | | | | |
| Hydroxypropyl guar gum | | 1 | 1 | 1 | 1 |
| "Gufquat 734" (trade name; product of ISP Japan) | 1 | | 1 | | |
| "Catinal LC100" (trade name;product of Toho Chemical Industry) | 1 | | | | 1 |
| "Polyether-modified silicone KF6005" trade name; (product of Shin-Etsu Chemical) | | | | | 0.4 |
| "Amodimethicone SM8702C" (product of Dow Corning Toray Silicone) | | | | 1.5 | |
| Monoethanol amine | | | 0.1 | | |
| Phosphoric acid | | | Amount to adjust pH to 9 | | |
| Perfume | | | q.s. | | |
| Water | | | Balance | | |

Examples 6 to 9

In a manner known per se in the art, the hair dye compositions as shown in Table 2 were prepared.

TABLE 2

| (wt. %) | | | Example 6 | 7 | 8 | 9 |
|---|---|---|---|---|---|---|
| 1st part | Dye [Compound (g)] | | 0.2 | 0.1 | | |
| | Dye [Compound (e)] | | | 0.1 | 0.15 | |
| | Dye [Compound (d)] | | | | | 0.2 |
| | Dye [Compound (k)] | | | | 0.1 | |
| | 28 wt. % Aqueous ammonia | | | 5 | | |
| | Monoethanolamine | | | 2 | | |
| | Propylene glycol | | | 8 | | |
| | Polyoxyethylene (20) isostearyl ether | | | 24 | | |
| | Polyoxyethylene (2) isostearyl ether | | | 20 | | |
| | "Merquat 280" (trade name; product of Calgon Corp., 35 wt.% aqueous solution) | | 8 | | | |
| | "Polymer JR400" (trade name; product of Union Carbide) | | | 0.5 | | 0.5 |
| | "Amodimethicone SM8702C" (trade name; product of Dow Corning Toray Silicone) | | | | 2 | |
| | "Polyether modified silicone KF6005" (trade name; product of Shin-Etsu Chemical) | | | | | 0.3 |
| | Tetrasodium ethylenediaminetetra acetate | | | | 0.1 | |
| | Perfume | | | | q.s. | |
| | Ammonium chloride | | | | Amount to adjust pH to 10 | |
| | Water | | | | Balance | |
| 2nd part | 35 wt. % Aqueous hydrogen peroxide | | | | 17.1 | |
| | Methylparaben | | | | 0.1 | |
| | Phosphoric acid | | | | Amount to adjust pH to 3.5 | |
| | Water | | | | Balance | |

Examples 10 to 12

In a manner known per se in the art, the hair dye compositions as shown in Table 3 were prepared.

TABLE 3

| (wt. %) | | Examples 10 | 11 | 12 |
|---|---|---|---|---|
| 1st part | Toluene-2,5-diamine | 2 | 1 | |
| | Para-aminophenol | | | 1 |
| | Resorcin | 0.9 | 1.1 | |
| | Para-amino-ortho-cresol | 0.5 | | 1.1 |
| | 2,4-Diaminophenoxyethanol | 0.7 | | |
| | Dye [Compound (i)] | 0.05 | | |
| | Dye [Compound (h)] | | 0.15 | |
| | Dye [Compound (c)] | | | 0.1 |
| | 28 wt. % Aqueous ammonia | | 5 | |
| | Monoethanolamine | | | 2 |
| | Propylene glycol | | | 8 |

TABLE 3-continued

|  | (wt. %) | Examples | | |
|---|---|---|---|---|
|  |  | 10 | 11 | 12 |
|  | Polyoxyethylene (20) isostearyl ether |  | 24 |  |
|  | Polyoxyethylene (2) isostearyl ether |  | 20 |  |
|  | "Merquat 280" (trade name; product of Calgon Corp., a 35 wt. % aqueous solution) | 8 |  |  |
|  | "Polymer JR400" (trade name; product of Union Carbide) |  | 0.5 |  |
|  | "Amodimethicone SM8702C" (trade name; product of Dow Corning Toray Silicone) |  |  | 2 |
|  | Sodium sulfite |  | 0.05 |  |
|  | Ascorbic acid |  | 0.5 |  |
|  | Tetrasodium ethylenediaminetetraacetate |  | 0.1 |  |
|  | Perfume |  | q.s. |  |
|  | Ammonium chloride |  | Amount to adjust pH to 10 |  |
|  | Water |  | Balance |  |
| 2nd part | 35 wt. % Aqueous hydrogen peroxide |  | 17.1 |  |
|  | Methylparaben |  | 0.1 |  |
|  | Phosphoric acid |  | Amount to adjust pH to 3.5 |  |
|  | Water |  | Balance |  |

Example 13

In a manner known per se in the art, the following hair dye composition was prepared.

|  | (wt. %) |
|---|---|
| (First part) |  |
| Para-aminophenol | 1 |
| Para-amino-ortho-cresol | 1.1 |
| Compound (b) | 0.1 |
| 28 wt. % Aqueous ammonia | 5 |
| Monoethanolamine | 2 |
| Cetanol | 8.5 |
| Polyoxyethylene (40) cetyl ether | 3 |
| Polyoxyethylene (2) cetyl ether | 3.5 |
| Stearyl trimethyl ammonium chloride | 2 |
| Liquid paraffin | 0.5 |
| Sodium sulfite | 0.05 |
| Ascorbic acid | 0.5 |
| Tetrasodium ethylenediaminetetraacetate | 0.1 |
| Perfume | q.s. |
| Ammonium chloride | Amount to adjust pH to 10 |
| Water | Balance |
| (Second part) |  |
| 35 wt. % Aqueous hydrogen peroxide | 17.1 |
| Methylparaben | 0.1 |
| Phosphoric acid | Amount to adjust pH to 3.5 |
| Water | Balance |

What is claimed is:

1. A method of dyeing hair, which comprises: applying a hair dye composition formulated as a two part composition, a first part containing a direct dye compound represented by the following formula (1), (2), (3) or (4):

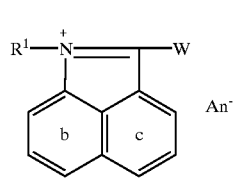

(1)

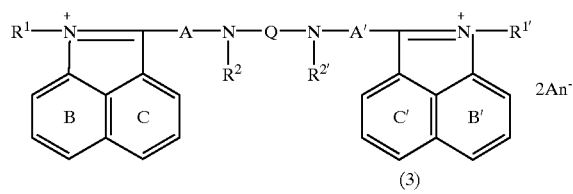

(2)

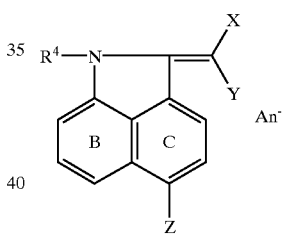

(3)

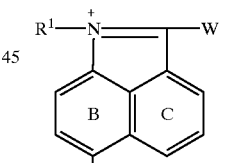

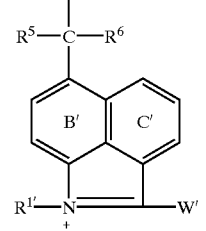

(4)

wherein, $R^1$ and $R^{1'}$ each independently represents a $C_{1-6}$ alkyl group which may have a substituent or an aryl group which may have a substituent, with the proviso that when the direct dye is a compound of formula (4), at least one of $R^1$ and $R^{1'}$ must be an aryl group which may have a substituent;

W and W' each independently represents a group —A—NR²R³ or a heterocyclic aromatic group which may have a substituent;

A and A' each independently represents a divalent aryl group which may have a substituent;

$R^2$, $R^{2'}$ and $R^3$ each independently represents a hydrogen atom, a $C_{1-6}$ alkyl group which may have a substituent or an aryl group which may have a substituent; or $R^2$, $R^{2'}$ or $R^3$ may be bonded to A or A', thereby fanning a nitrogen-containing heterocycle, $R^2$ and $R^3$ are coupled to form a nitrogen-containing heterocycle, together with the adjacent nitrogen atom, or $R^2$ and $R^{2'}$ are coupled to form a nitrogen-containing heterocycle together with the adjacent two nitrogen atoms and Q;

$R^4$, $R^5$ and $R^6$ each independently represents a hydrogen atom, a $C_{1-6}$ alkyl group which may have a substituent or a $C_{1-6}$ alkenyl group which may have a substituent;

Q represents a divalent organic connecting group;

X represents a modified carboxy group, an —SO₂—T-group (in which, T represents a $C_{1-4}$ alkyl group, $C_{2-4}$ alkenyl group or an aryl group) or a heterocyclic group;

Y represents a cyano group or a heterocyclic group;

Z represents a cationic group, rings b, c, B, C, B' and C' may each have a substituent other than that described directly in the formula, or when in the formula (1), $R^1$ represents a $C_{1-6}$ alkyl group and W represents a group —A—NR²R³ (except that $R^2$ or $R^3$ is bonded to A to form a nitrogen-containing group), any one of the rings b, c and A has at least one substituent; and An⁻ represents an anion; and a second part comprising an oxidizing agent in admixture to the hair.

2. The method according to claim 1, wherein said first part comprises one or more direct dyes other than said dye of formula (1), (2), (3) or (4).

3. The method according to claim 1, wherein said compound of formula (1), (2), (3) or (4) is present in the composition in an amount of 0.01 to 20 wt. % based on the weight of the composition.

4. The method according to claim 3, wherein said compound of formula (1), (2), (3) or (4) is present in the composition in an amount of 0.05 to 10 wt. % based on the weight of the composition.

5. The method according to claim 4, wherein said compound of formula (1), (2), (3) or (4) is present in the composition in an amount of 0.1 to 5 wt. % based on the weight of the composition.

6. The method according to claim 2, wherein the total amount of said direct dyes is from 0.05 to 10 wt. %, based on the weight of the composition.

7. The method according to 6, wherein the total amount of dye ranges from 0.1 to 5 wt. %, based on the weight of the composition.

8. The method according to claim 1, wherein the composition has a pH of 6 to 11.

9. The method according to claim 8, wherein the composition has a pH of 8 to 11.

10. The method according to claim 1, wherein the oxidizing agent is hydrogen peroxide.

11. The method according to claim 1, wherein the oxidizing agent is present in the composition in an amount of 0.5 to 10 wt. % based on the weight of the composition.

12. The method according to claim 11, wherein the oxidizing agent is present in the composition in an amount of 1 to 8 wt. % based on the weight of the composition.

13. The method according to claim 1, wherein said first part is comprised of an oxidation dye of at least a color developer and a coupler, each being present in the composition in an amount of 0.01 to 20 wt. % based on the weight of the composition.

14. The method according to claim 13, wherein said amount of oxidation dye ranges in amount from 0.5 to 10 wt. % based on the weight of the composition.

15. A method of dyeing hair, which comprises: applying a hair dye composition formulated as a one part composition comprising a direct dye compound represented by the following formula (1), (2), (3) or (4):

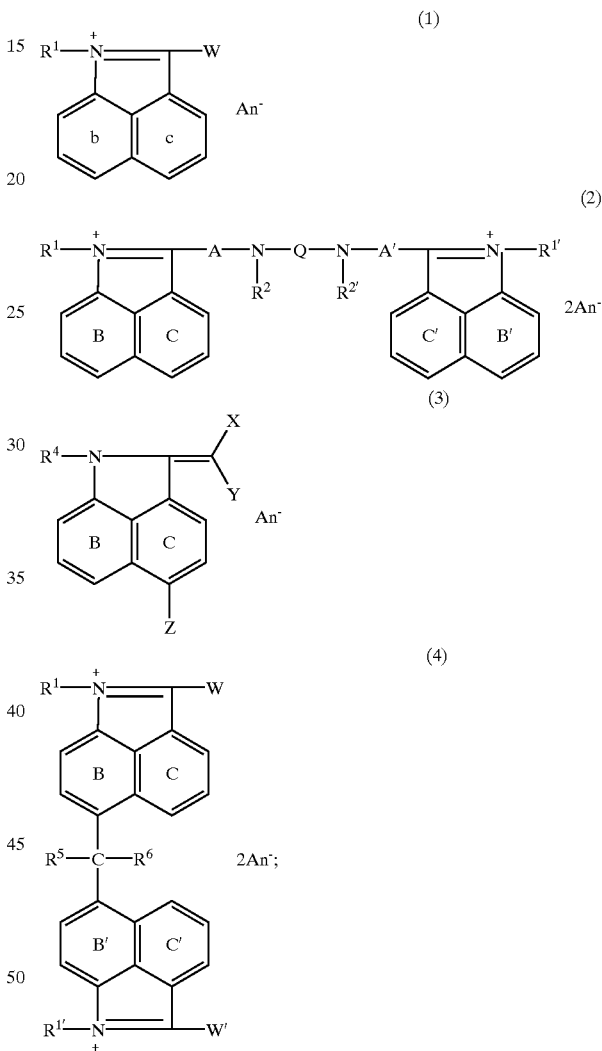

wherein, $R^1$ and $R^{1'}$ each independently represents a $C_{1-6}$ alkyl group which may have a substituent or an aryl group which may have a substituent;

W and W' each independently represents a group —A—NR²R³ or a heterocyclic aromatic group which may have a substituent;

A and A' each independently represents a divalent aryl group which may have a substituent;

$R^2$, $R^{2'}$ and $R^3$ each independently represents a hydrogen atom, a $C_{1-6}$ alkyl group which may have a substituent or an aryl group which may have a substituent; or $R^2$, $R^{2'}$ or $R^3$ may be bonded to A or A', thereby forming a nitrogen-containing heterocycle, $R^2$ and $R^3$ are coupled to form a nitrogen-containing heterocycle, together with the adjacent nitrogen atom, or $R^2$ and $R^{2'}$ are coupled to form a nitrogen-containing heterocycle together with the adjacent two nitrogen atoms and Q;

$R^4$, $R^5$ and $R^6$ each independently represents a hydrogen atom, a $C_{1-6}$ alkyl group which may have a substituent or a $C_{1-6}$ alkenyl group which may have a substituent;

Q represents a divalent organic connecting group;

X represents a modified carboxy group, an —$SO_2$—T- group (in which, T represents a $C_{1-4}$ alkyl group, $C_{2-4}$ alkenyl group or an aryl group) or a heterocyclic group;

Y represents a cyano group or a heterocyclic group;

Z represents a cationic group, rings b, c, B, C, B' and C' may each have a substituent other than that described directly in the formula, or when in the formula (1), $R^1$ represents a $C_{1-6}$ alkyl group and W represents a group —A—$NR^3R^3$ (except that $R^2$ or $R^3$ is bonded to A to form a nitrogen-containing group), any one of the rings b, c and A has at least one substituent; and An⁻ represents an anion; the composition having a pH ranging from 6–11 that is adjusted to within said range by an alkali agent and containing at least one cosmetic ingredient selected from the group consisting of hydrocarbons, animal or vegetable fats and oils, fatty acids, organic solvents, hair penetration promoters, cationic surfactants, natural or synthetic polymers, alcohols, ethers, amphoteric surfactants, nonionic surfactants, protein derivatives, amino acids, antiseptics, chelating agents, stabilizing agents, antioxidants, plant extracts, crude drug extracts, vitamins, colorants, perfumes, aerosolizing agents and UV absorbers, to the hair.

16. A method of dyeing hair, which comprises: applying a hair dye composition formulated as a three part composition, a first part containing a direct dye compound represented by the following formula (1), (2), (3) or (4):

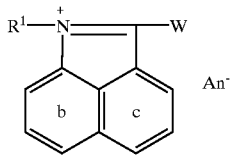
(1)

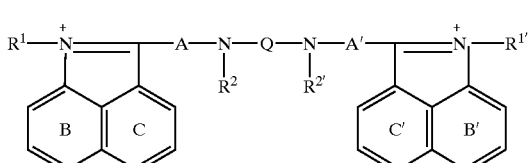
(2)

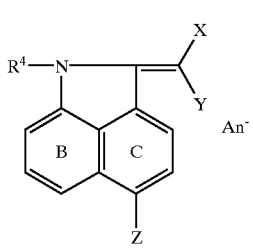
(3)

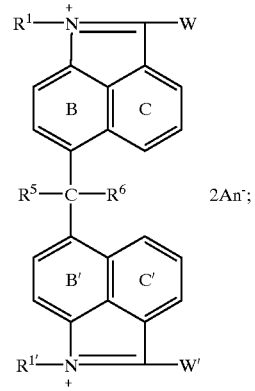
(4)

wherein, $R^1$ and $R^{1'}$ each independently represents a $C_{1-6}$ alkyl group which may have a substituent or an aryl group which may have a substituent;

W and W' each independently represents a group —A—$NR^2R^3$ or a heterocyclic aromatic group which may have a substituent;

A and A' each independently represents a divalent aryl group which may have a substituent;

$R^2$, $R^{2'}$ and $R^3$ each independently represents a hydrogen atom, a $C_{1-6}$ alkyl group which may have a substituent or an aryl group which may have a substituent; or $R^2$, $R^{2'}$ or $R^3$ may be bonded to A or A', thereby forming a nitrogen-containing heterocycle, $R^2$ and $R^3$ are coupled to form a nitrogen-containing heterocycle, together with the adjacent nitrogen atom, or $R^2$ and $R^{2'}$ are coupled to form a nitrogen-containing heterocycle together with the adjacent two nitrogen atoms and Q;

$R^4$, $R^5$ and $R^6$ each independently represents a hydrogen atom, a $C_{1-6}$ alkyl group which may have a substituent or a $C_{1-6}$ alkenyl group which may have a substituent;

Q represents a divalent organic connecting group;

X represents a modified carboxy group, an —$SO_2$—T- group (in which, T represents a $C_{1-4}$ alkyl group, $C_{2-4}$ alkenyl group or an aryl group) or a heterocyclic group;

Y represents a cyano group or a heterocyclic group;

Z represents a cationic group, rings b, c, B, C, B' and C' may each have a substituent other than that described directly in the formula, or when in the formula (1), $R^1$ represents a $C_{1-6}$ alkyl group and W represents a group —A—$NR^2R^3$ (except that $R^2$ or $R^3$ is bonded to A to form a nitrogen-containing group), any one of the rings b, c and A has at least one substituent; and An⁻ represents an anion;

a second part comprising an oxidizing agent selected from the group consisting of hydrogen peroxide, a perborate, a percarbonate and a bromate; and a third part of a powdered persulfate, in admixture to the hair.

17. A method of dyeing hair, which comprises: applying a hair dye composition comprising, as a direct dye, a compound represented by the following formula (1), (2), (3) or (4):

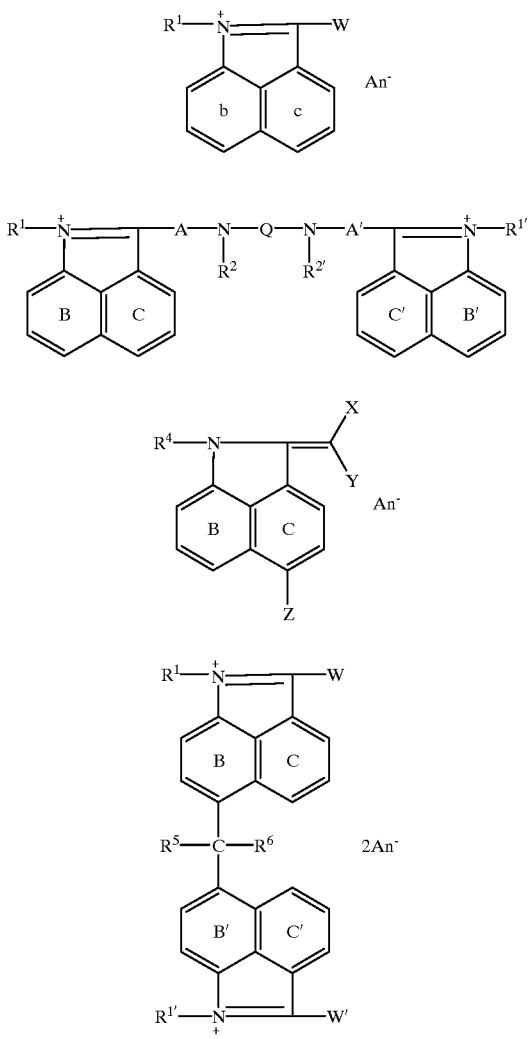

wherein, $R^1$ and $R^{1'}$ each independently represents a $C_{1-6}$ alkyl group which may have a substituent or an aryl group which may have a substituent, with the proviso that when the direct dye is a compound of formula (4), at least one of $R^1$ and $R^{1'}$ must be an aryl group which may have a substituent;

W and W' each independently represents a group —A—$NR^2R^3$ or a heterocyclic aromatic group which may have a substituent;

A and A' each independently represents a divalent aryl group which may have a substituent;

$R^2$, $R^{2'}$ and $R^3$ each independently represents a hydrogen atom, a $C_{1-6}$ alkyl group which may have a substituent or an aryl group which may have a substituent; or $R^2$, $R^{2'}$ or $R^3$ may be bonded to A or A', thereby forming a nitrogen-containing heterocycle, $R^2$ and $R^3$ are coupled to form a nitrogen-containing heterocycle, together with the adjacent nitrogen atom, or $R^2$ and $R^{2'}$ are coupled to form a nitrogen-containing heterocycle together with the adjacent two nitrogen atoms and Q;

$R^4$, $R^5$ and $R^6$ each independently represents a hydrogen atom, a $C_{1-6}$ alkyl group which may have a substituent or a $C_{1-6}$ alkenyl group which may have a substituent;

Q represents a divalent organic connecting group;

X represents a modified carboxy group, an —$SO_2$—T-group (in which, T represents a $C_{1-4}$ alkyl group, $C_{2-4}$ alkenyl group or an aryl group) or a heterocyclic group;

Y represents a cyano group or a heterocyclic group;

Z represents a cationic group, rings b, c, B, C, B' and C' may each have a substituent other than that described directly in the formula, or when in the formula (1), $R^1$ represents a $C_{1-6}$ alkyl group and W represents a group —A—$NR^2R^3$ (except that $R^2$ or $R^3$ is bonded to A to form a nitrogen-containing group), any one of the rings b, c and A has at least one substituent; and $An^-$ represents an anion;

to the hair.

* * * * *

UNITED STATES PATENT AND TRADEMARK OFFICE
CERTIFICATE OF CORRECTION

PATENT NO.    : 6,605,125 B2
DATED         : August 12, 2003
INVENTOR(S)   : Hajime Miyabe et al.

It is certified that error appears in the above-identified patent and that said Letters Patent is hereby corrected as shown below:

Column 19,
Line 9, "thereby fanning" should read -- thereby forming --.

Signed and Sealed this

Twenty-eighth Day of October, 2003

JAMES E. ROGAN
*Director of the United States Patent and Trademark Office*